(12) United States Patent
Birnbach

(10) Patent No.: US 8,682,596 B2
(45) Date of Patent: Mar. 25, 2014

(54) METHOD AND SYSTEM FOR DETECTING MATERIALS

(75) Inventor: Curtis A. Birnbach, New Rochelle, NY (US)

(73) Assignee: Advanced Fusion Systems LLC, Newton, CT (US)

( * ) Notice: Subject to any disclaimer, the term of this patent is extended or adjusted under 35 U.S.C. 154(b) by 73 days.

(21) Appl. No.: 13/027,137

(22) Filed: Feb. 14, 2011

(65) Prior Publication Data

US 2011/0201510 A1 Aug. 18, 2011

Related U.S. Application Data

(60) Provisional application No. 61/304,318, filed on Feb. 12, 2010.

(51) Int. Cl.
*G01N 31/00* (2006.01)

(52) U.S. Cl.
USPC .................................. 702/27; 702/22; 702/23

(58) Field of Classification Search
None
See application file for complete search history.

(56) References Cited

U.S. PATENT DOCUMENTS

| | | |
|---|---|---|
| 4,596,967 A | 6/1986 | Ekdahl |
| 4,661,783 A | 4/1987 | Gover et al. |
| 4,950,962 A | 8/1990 | Birnbach |
| 7,916,507 B2 | 3/2011 | Birnbach |
| 2003/0151366 A1 | 8/2003 | Dayton, Jr. |
| 2008/0060455 A1 | 3/2008 | Coyle |
| 2008/0063132 A1 | 3/2008 | Birnbach |
| 2009/0190383 A1 | 7/2009 | Birnbach |

FOREIGN PATENT DOCUMENTS

WO 2009094589 A1 7/2009

OTHER PUBLICATIONS

S.J. Smith, E.M. Purcell, Visible Light from Localized Surface Charges Moving Across a Grating, Phys Rev, p. 1069 vol. 92.
Herbert M. Pickett, THz spectroscopy of the atmosphere, Terahertz Spectroscopy and Applications (Proceedings Volume), vol. 3617, Apr. 29, 1999.
Bradley Fegruson and Xi-Cheng Zhang, Materials for terahertz science and technology, Nature Materials, Sep. 2002, p. 26, vol. 1.
Cuesta et al., Determination of carbendazim, fuberidazole and thiabendazole by three-dimensional excitation-emission matrix fluorescence and parallel factor analysis, Jun. 2003.

*Primary Examiner* — Eric S Dejong
(74) *Attorney, Agent, or Firm* — Charles E. Bruzga; Bruzga and Associates

(57) ABSTRACT

Disclosed is a method for detecting one or both of the native material in an object and any foreign material in the object by parallel-mode spectroscopy, comprising parallel-mode data acquisition, signal processing and data reduction and providing results. Parallel-mode data acquisition comprises producing an interrogating signal simultaneously containing electromagnetic radiation of sufficient bandwidth in the range of approximately 10 GHz to approximately 25 THz to allow simultaneous detection of a plurality of signals at a plurality of frequencies, each signal being at some amplitude, which collectively provide a unique spectral signature of a material whose detection is desired. The signal processing and data reduction comprises processing a signal resulting from exposing the object to the interrogating radiation to produce a three-dimensional data matrix representative of at least any foreign or native material associated with the object. Correlation technique is used to compare the data matrix to a reference library.

19 Claims, 13 Drawing Sheets

METHOD AND SYSTEM FOR DETECTING MATERIALS

CROSS-REFERENCE TO RELATED APPLICATION

This application claims priority from U.S. Provisional Patent Application No. 61/304,318, filed 12 Feb. 2010. The foregoing application is incorporated herein by reference, in its entirety.

FIELD OF THE INVENTION

The present invention relates to a method and system for detecting the presence of materials native or foreign to an object, and more particularly to a method and system that uses parallel-mode spectroscopy to increase rapidity of detection.

BACKGROUND OF THE INVENTION

There is a substantial need for high-speed, non-invasive methods of analyzing or screening persons and other objects for the presence of foreign or native materials. Foreign materials include but are not limited to—

Explosives and their precursors and intermediaries
Chemicals and their precursors and intermediaries
Pharmaceuticals and their precursors and intermediaries
Chemical and Biological Weapons and their precursors and intermediaries
Bacterial, Viral and other life-forms Intended native materials include that may have been intermixed with foreign material but are not limited to—

Pharmaceuticals and their precursors and intermediaries
Chemicals and their precursors and intermediaries
Foods and Food Products and their precursors and intermediaries There have been a number of attempts to produce analysis and screening techniques that addresses the foregoing requirement with respect to analyzing objects for the presence of foreign material, but for one reason or another, such attempts have all been inadequate. Examples include backscatter X-ray, neutron activation, mass spectroscopy (several varieties), and mmWave Imaging. These techniques either use ionizing radiation, rely on detection of vapors, or use intrusive imaging techniques that, while capable of "seeing" through clothes, are still severely limited and susceptible of providing false positive or false negative results.

Prior art in mmWave technology has consisted of imaging systems, which have been somewhat controversial. The controversy arises because the operator of the system is given the ability to "see through" peoples' clothes to determine if there is anything hidden. Many people find these devices to be highly invasive of their privacy. Additionally, their limited ability to discern various types of explosives or contraband is a serious drawback.

Another area of interest is the detection of airborne contagious diseases. One of the biggest threats faced by a society with extensive global travel enabled by large capacity jet airplanes is the susceptibility to airborne diseases. An air traveler on a trip with two or more connecting flights can expose a potentially huge number of people to a contagious disease, thus making the source of the disease extremely difficult to trace while simultaneously risking an epidemic spread of the disease. Obviously, air travelers on a direct flight with a contagious disease still pose a significant risk, since many passengers would still be exposed to the disease before and during the flight, and then those exposed passengers would expose other persons during their ensuing contagious incubation period.

Spectroscopy has many advantages as an analytical and screening technique, but as typically practiced suffers from being a slow process due to acquiring data in a serial manner. It would be desirable to have a spectroscopic method and system capable of near real-time operation for screening purposes such as those described above. There are many applications for such a system for detecting foreign materials on, or in, an object. Examples of materials foreign to an object are explosives or components of explosives, contraband, chemical and biological weapons, pharmaceuticals, contaminants in food being processed, contaminants in legitimate chemical products, and materials associated with disease in humans and animals.

BRIEF SUMMARY OF THE INVENTION

In a preferred form, in connection with an object having native material and potentially having foreign material, the present invention provides a method for detecting one or both of the native material and the foreign material by parallel-mode spectroscopy. The method comprises (1) parallel-mode data acquisition, (2) signal processing and data reduction and (3) providing results. Parallel-mode data acquisition comprises producing an interrogating signal simultaneously containing electromagnetic radiation of sufficient bandwidth in the range of approximately 10 GHz to approximately 25 THz to allow simultaneous detection of a plurality of signals at a plurality of frequencies, each signal being at some amplitude, which collectively provide a unique spectral signature of a material whose detection is desired. The object and any associated foreign material are exposed to the interrogating signal so as to cause interaction between the signal and the object and any associated foreign material. A modified signal resulting from the interaction of the interrogating signal with the object and any associated foreign material is detected. The signal processing and data reduction comprises processing the resulting signal to produce a three-dimensional data matrix representative of at least any foreign or native material associated with the object. A reference library of data representing known chemical or biological materials of interest is provided. Correlation technique is used to compare the data matrix to the reference library, to produce at least one correlation peak corresponding to at least one associated foreign or native material from the reference library data. The results of the foregoing comparison are provided.

The foregoing method provides a spectroscopic method that can be made capable of near real-time operation for detecting materials foreign or native to an object.

DETAILED DESCRIPTION OF THE INVENTION

Figure 1:
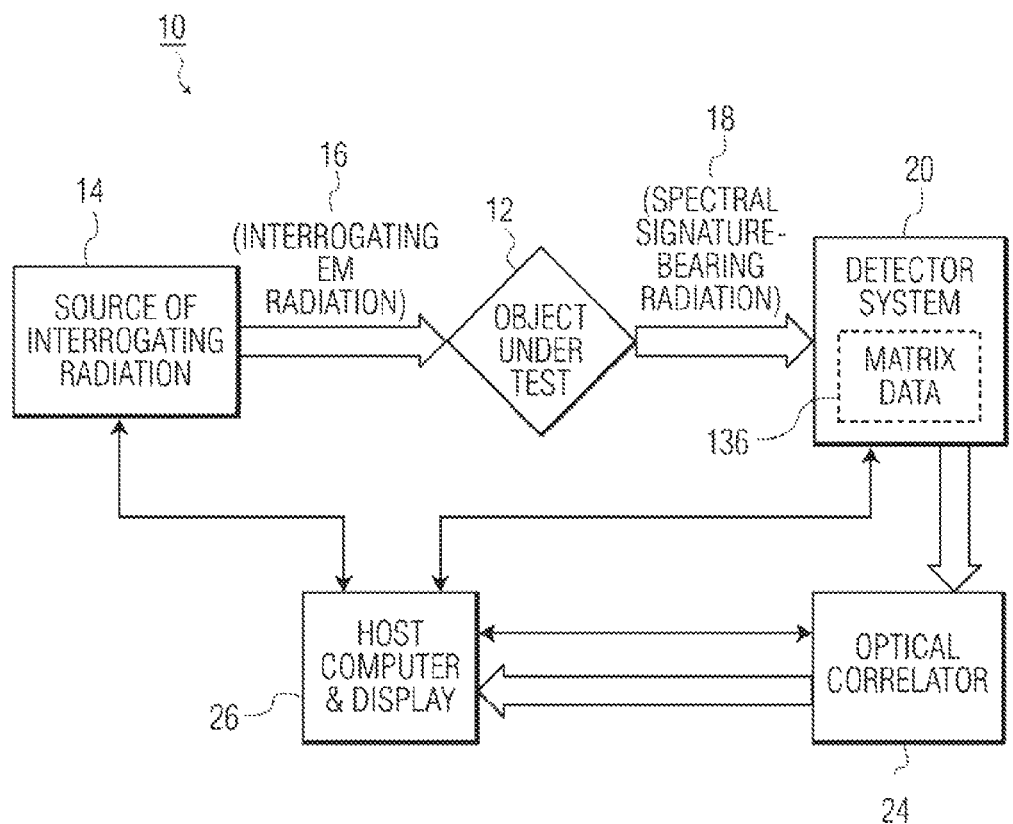
FIG. 1 shows a block diagram of a preferred system for implementing the present invention.

Various definitions as used herein are as follows:

DEFINITIONS

Interrogating Radiation Source: By "interrogating radiation source" is meant herein broadband electromagnetic radiation simultaneously containing electromagnetic radiation of sufficient bandwidth in the range of approximately 10 GHz to approximately 25 THz to allow simultaneous detection of a plurality of signals at a plurality of frequencies, each signal being at some amplitude, which collectively provide a unique spectral signature of a material whose detection is desired.

Broadband: An expression of the bandwidth of a signal relative to its center frequency. "Broadband" is defined herein as being a signal whose frequency is greater than about 25% of the center frequency relative to the highest frequency.

Foreign Material: As used herein, a "foreign material" is one that is undesirably associated with an object. Examples of foreign materials are: explosives, illegal drugs, chemical and biological agents, food contaminants, chemical contaminants, pharmaceutical contaminants, materials associated with diseases, and Pathogens including but not limited to viruses, bacteria, proteins, prions, fungi and spores. Foreign material may have multiple constituents, whereby the spectral signature that is obtained reflects the multiple constituents and the amounts of each.

Material: As used herein, "material" may constitute a singular substance or plural substances.

Object: As used herein, an "object" connotes an entity that may or may not have a foreign material associated with it. Examples of objects in this context include, but are not limited to: people, people and clothing or luggage, food, vehicles, pharmaceuticals, chemicals, animals and biological entities. An "object" may be a single entity (e.g., person) or may comprise multiple entities (a person wearing clothing).

Native Material: As used herein, "native material" connotes the material from which an object, as defined above, is composed, excluding foreign material. Native material may have multiple constituents, whereby the spectral signature that is obtained reflects the multiple constituents and the amounts of each. An example concerns an object comprising a person and that person's clothing, wherein both the person and that person's clothing are innocuous when screening for explosives. Another example concerns an object comprising an automobile, which has many innocuous components that are considered native when screening for explosives.

Foreign or Native Material: As used herein, "foreign or native material" or similar phrases means either or both of foreign and native material, except when the context requires otherwise.

Having: When used in reference to an object "having" a foreign or native material, it is meant herein that the object directly or indirectly physically supports or incorporates such material. For instance, a foreign material may consist of an explosive reactant contained in the clothing of a person wherein the person and any innocuous clothing of the person (1) together comprise an object under test and (2) are considered native when screening for explosives. Other examples include the material being contained within the object itself, such as the foreign material of a bacteria or virus being contained within the human body, or a contaminant such as salmonella being contained within a piece of red meat or chicken Resonant interrogating signal: As used herein, a resonant interrogating signal is one where one or more frequencies of the interrogating signal are at resonance frequencies of a potentially present foreign material. Such resonance frequencies may be associated with vibrational, rotational or other known molecular transitions of, for instance, a potentially present foreign material.

Overall System Configuration

FIG. 1 shows a system 10 for detecting foreign material or native material by parallel-mode spectroscopy in connection with an object 12 under test having native material and potentially having a foreign material. In general overview, a source 14 of interrogating radiation is used to expose object 12 under test to interrogating electromagnetic ("EM") radiation 16. After passing through object 12, such radiation 18 bears a spectral signature of the object and, if desired, of any foreign material, if present, that is then detected by detector system 20. An optical correlator 24 performs various functions, including signal pre-processing, correlation preferably using subtraction, and threshholding; these operations are undertaken for the purpose of distinguishing the spectral signatures of the object and of native material and of any foreign materials present. A host computer 26 interacts with the source 14 of Interrogating radiation, the detector system 20 and the optical correlator 24, and also provides a display of output data.

MODES OF OPERATION

As will be described in more detail below, the system of FIG. 1 can be operated in various modes, including but not limited to:

Foreign material analysis mode. In this mode, an object 12 under test is analyzed to determine whether foreign material is present in the object and in what quantity or quantities by comparison with a reference spectral signature from a library.

Native material screening mode. In this mode, an object 12 under test is screened to determine whether native material is present in the object and in what quantity or quantities by comparison with a reference spectral signature from a library. A subset of this mode involves comparison of an object 12 under test with a known, reference object that should lack foreign material.

Sequential modes of operation. The inventive system (e.g., FIG. 1) can be operated in sequential modes. One example of sequential modes is to first compare an object 12 with a reference object, as mentioned just above, followed by a foreign material analysis mode of operation if the object does not match the reference object.

A simultaneous analyses mode. This mode provides for analyzing or screening an object 12 under test for both native and foreign materials. "Simultaneous" as used in "simultaneous analyses mode" refers to the simultaneity of interrogating the object for native and foreign materials at the same time, and does not relate the subsequent optical correlation process undertaken by the optical correlator 24 which, of necessity, must be conducted in a serial fashion.

Fluorescence mode. In this mode, detection of foreign or native material is undertaken by interrogating the object 12 under test with a first frequency known to excite secondary radiation at a second resonant frequency in foreign or native material that resonates at such second resonant frequency. In such mode, typically only the signals at the second resonant frequency or frequencies are the subject of detection.

Learning mode. In this mode, the inventive system (e.g., 10, FIG. 1) analyses or scans known material for the purpose of creating a library of matrix data for use in analyzing or screening subsequent objects, or adding to a preexisting library of matrix data.

The following description elaborates on the FIG. 1 block diagram of a preferred embodiment of the current invention in the following topics:

Interrogating radiation source 14
Object 12 to be tested
Detector System 20
The functions of the optical correlation processor 24 of—
Signal re-processing
Correlation
Subtraction
Thresholding
Providing output data by the host computer & display 26

Interrogating Radiation Source 14

Figure 2:
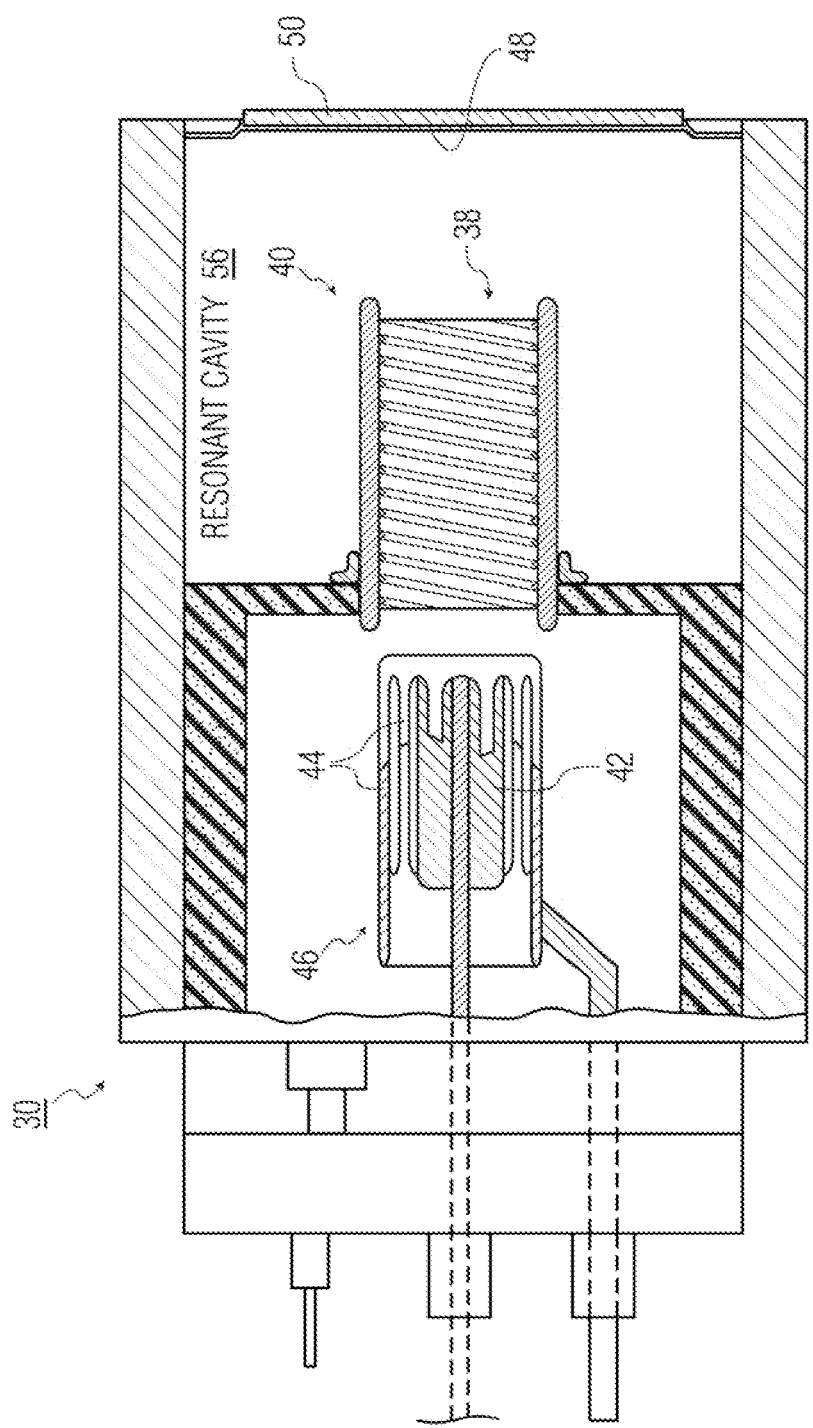
FIG. 2 shows a mostly cross-sectioned view of the Cylindrical Smith-Purcell enhanced Magnetically Insulated Linear Oscillator that may be used in the source of interrogating radiation of FIG. 1, with the grid 44 shown partially cut-away.

With reference to FIG. 1, the object 12 and any foreign material to be tested are exposed to an interrogating signal from a broadband source 14 of interrogating radiation as defined above so that the interrogating signal interacts with the object. FIG. 2 shows a preferred apparatus 30 for source 14 of interrogating radiation, which is a Magnetically Insulated Linear Oscillator enhanced with a Cylindrical Smith-Purcell structure. Such structure is most correctly defined herein as a Cylindrical Smith-Purcell enhanced Magnetically Insulated Linear Oscillator 30 (CSP-MILO), and is described in some detail as follows. Further details of apparatus 30 of FIG. 2 are discussed below.

Figure 3:
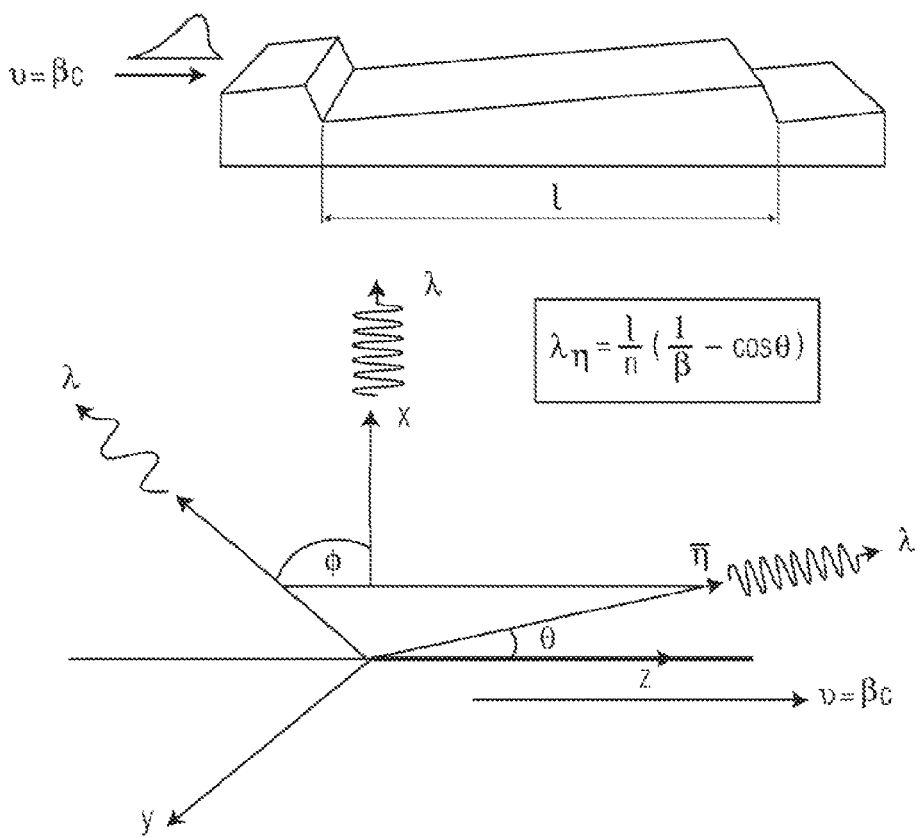
FIG. 3 shows a prior art rendition of the Smith-Purcell RF generation process.

The Smith-Purcell effect was first described in S. J. Smith and E. M. Purcell, Visible Light from Localized Surface Charges Moving across a Grating, Phys Rev 92, 1069 (1953). Smith and Purcell have taught that when an electron passes close to the surface of a metal diffraction grating, moving at right angles to the rulings, the periodic motion of the charge induced on the surface of the grating should give rise to radiation. FIG. 3 shows the Smith-Purcell RF generation process and is derived from the foregoing article. In particular, this figure shows a simple Huygens construction wherein the fundamental wavelength is $l(1/\beta - \cos \Theta)$, $l$ is the distance between rulings, $\beta$ stands for $v/c$ as usual (where $v$ is the velocity of the electron beam and $c$ is the speed of light), and $\Theta$ is the angle between the direction of motion of the electron and the light ray.

Figure 4:
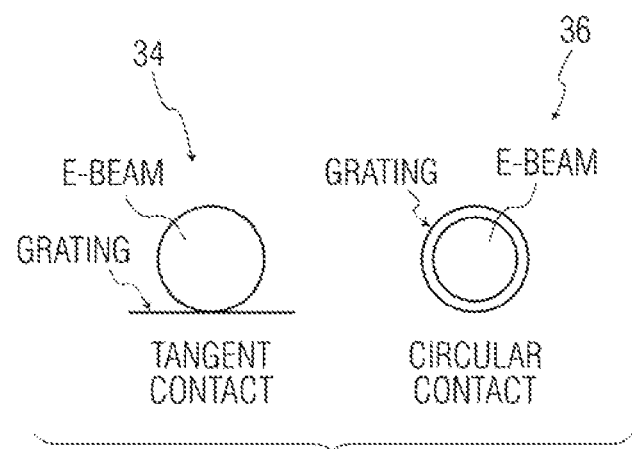
FIG. 4 shows in simplified form the relationship of an electron beam to planar and cylindrical gratings for the purposes of Smith-Purcell RF generation in connection with the source of interrogating radiation of FIG. 2.

It was realized by the present inventor that the Smith-Purcell Effect was not overly efficient, due to the limited number of electrons that are brought into appropriate proximity of the grating surface due to the tangent geometry described by Smith and Purcell. FIG. 4 shows the relationship of the electron beam to a planar surface (prior art) in arrangement 34, and alternatively to cylindrical gratings in arrangement 36, for the purposes of Smith-Purcell RF generation. Since FIG. 4 is simplified, it is important to note that the electron beam (E-beam) contacts the entire inner surface of a cylindrical grating. The Cylindrical Smith-Purcell variant, as described by the current inventor in US Patent Application Publication No. 2008/0063132 A1 has the following significant advantage: With reference to the cross-sectional views of FIGS. 2, 7 and 8, the entire surface of the electron beam in contact with the inner surface of a cylindrical grating 38 ruled on the interior surface of a drift tube 40. This increases the efficiency of generating RF by orders of magnitude in comparison to a conventional planar Smith-Purcell device. It is noted that by placing an appropriate electrical charge on the drift tube 40 (FIGS. 2, 7 and 8), the electron beam may be drawn into intimate contact with the surface of cylindrical grating 38 on the interior of the drift tube. The voltage required is proportional to the voltage used to form the electron beam.

Referring to FIG. 2, an electron beam is formed by cathode 42 and grid 44 that form a Traveling Wave Electron Gun 46, and is accelerated towards an anode 48 on a trajectory that takes it through the enhanced drift tube. A window 50, transparent to RF radiation, for instance, overlies anode 48 and provides a vacuum seal as well as a means for allowing the RF to exit from the CSP-MILO apparatus 30. The beam outside diameter and drift tube/grating inner diameter are adjusted to be approximately the same, to ensure that the exterior surface of the beam is in intimate contact with the grating surface, but not so much that the grating is eroded by the electron beam. These points relate to the above description of FIG. 4.

Figure 5:
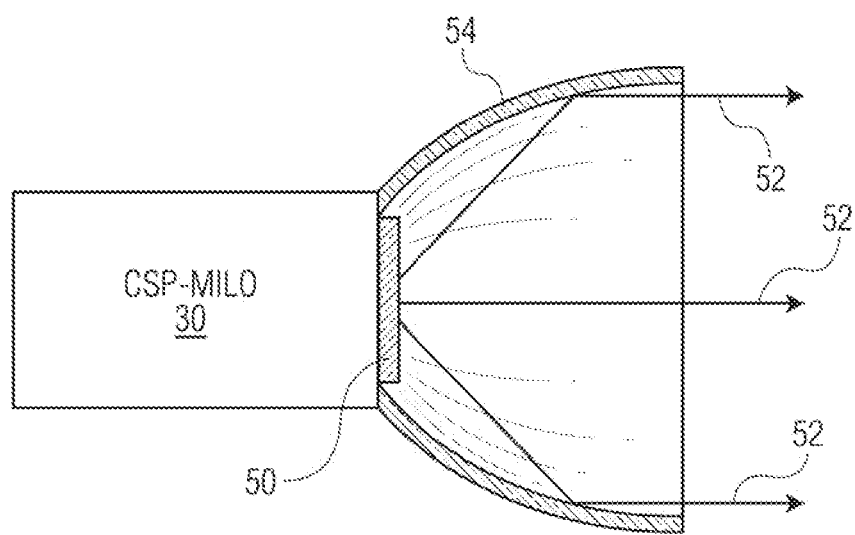
FIG. 5 show an off-axis reflective beam correction quasi-optical element that may be used in the system of FIG. 1, and is partially in block form and partially in cross section.

The electromagnetic beam produced by the structure described above is divergent. As shown in FIG. 5, this may be corrected to a partially or fully collimated, or focused, beam 52 by use of an off-axis parabolic type reflector 54. The beam correction is a quasi-optical process using the reflective element of the reflector 54.

Referring to FIG. 2, there is an additional interaction between the electron beam and the resonant cavity section 56 of the CSP-MILO apparatus 30. An oscillation occurs between the end of the electron gun 46 and the anode 48, causing the electrons to oscillate back and forth through the drift tube 40. This has the effect of (a) broadening the bandwidth, (b) establishing the lower frequency of the radiated RF, and (c) increasing the efficiency of the Smith-Purcell process by causing the electrons to repeatedly interact with the grating. RF is only emitted in one direction, through the window 50, due to the blaze angle of the grating.

The frequency of the CSP-MILO apparatus 30 can be controlled in two ways, (1) by a coarse adjustment and (2) by a fine adjustment. The coarse adjustment can be accomplished by controlling the size and geometry of grating 38 and the size of cavity 56 of apparatus 30. The fine adjustment can be accomplished by adjusting the high voltage in connection with the Smith-Purcell effect. The CSP-MILO apparatus 30 is preferably designed so that its output signal, or interrogating radiation 16 (FIG. 1), constitutes broadband electromagnetic radiation simultaneously containing electromagnetic radiation of sufficient bandwidth in the range of approximately 10 GHz to approximately 25 THz to allow simultaneous detection of a plurality of signals at a plurality of frequencies, each signal being at some amplitude, which collectively provide a unique spectral signature of a material whose detection is desired.

With regard to interrogating radiation 16 (FIG. 1), the frequency range above 1 THz provides a unique spectroscopic interrogating of the low frequency vibrational modes of materials. A wide variety of molecular properties, from the tertiary structure of proteins and polynucleotides to mechanisms of ozone depletion, can be characterized by their modal spectra. Such molecular-specific spectroscopy requires (a) spectral resolution at or below approximately 2 MHz, which provides parts per billion ($1 \times 10^9$) resolution, (b) a spectral range which extends to several THz, and (c) frequency tunability.

Figure 6:
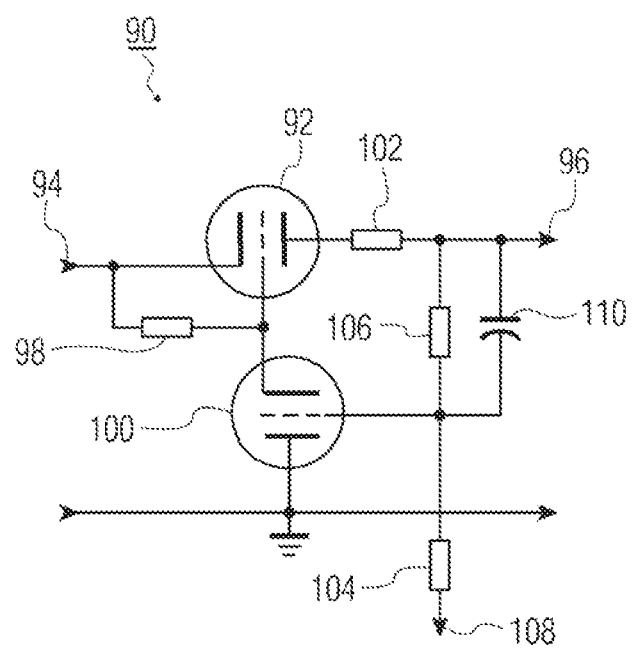
FIG. 6 shows a current regulator circuit implemented with cold-cathode field emission triodes that can be used in the source of interrogating radiation of the system of FIG. 1.

FIG. 6 shows a current regulator circuit 90 that may be used to regulate the power of the CSP-MILO apparatus 30 (FIG. 2) in a somewhat analogous way to the classic Two-FET (Field Effect Transistor) current regulator found in low voltage power supplies. In FIG. 6, current regulator circuit 90 is implemented with cold-cathode field emission triodes 92 and 100, either or both of which may comprise Pulsatron tubes, as disclosed in U.S. Pat. No. 4,950,962, entitled High Voltage Switch Tube, for example, by the present inventor and others. The problem addressed by current regulator circuit of FIG. 6 is that there are no solid state or conventional vacuum tube devices that are capable of operating in the voltage or current regimes contemplated for this design.

This circuit topology was disclosed by the present inventor in US Patent Application Publication No. 2009/0190383 A1, published on Jul. 30, 2009. Further details of current regulator circuit 90 are described below.

With reference to FIG. 2, a high voltage pulse is directly applied to the cathode 42 of the CSP-MILO apparatus 30. The body of the apparatus 30 forms a resonant cavity 56 which oscillates when the cathode fires. A grid 44 controls the firing of the CSP-MILO apparatus 30. A trigger pulse is applied to the grid 44 to initiate the RF generation process.

The CSP-MILO apparatus 30, considered by itself, is known and described in US Patent Application Publication No. 2008/0063132 A1, published Mar. 13, 2008, by the current inventor (C. A. Birnbach), and is a high power RF source. It incorporates drift tube 40 with a cylindrical grating 38 on its inner surface and uses a Traveling Wave Electron Gun (TWEG) 46 originally disclosed in U.S. Pat. No. 4,950,962 by C. A. Birnbach. Referring to FIG. 2, the dimensions of the resonant cavity 56 in conjunction with the dimensions of the drift tube 40 determine the output range. Conventional MILO devices, specifically those lacking the CSP structure, have outputs between 300 MHz and 3.5 GHz. The present inventor has experimentally verified that by placing an electromagnetic cylindrical grating 38 surface on the inner cylindrical face of the drift tube 40, as shown FIGS. 7 and 8, arranged so that the exterior surface of the electron beam is in intimate contact with the grating 38 on the inner surface of the drift tube, it is possible to generate RF at much higher frequencies than those available from a smooth-bore drift tube. The source of this RF is due to the Smith-Purcell effect as described above, which relates to the interaction of a relativistic electron beam with a grating surface. Outputs in frequencies well into the THz range are possible.

Figure 7:
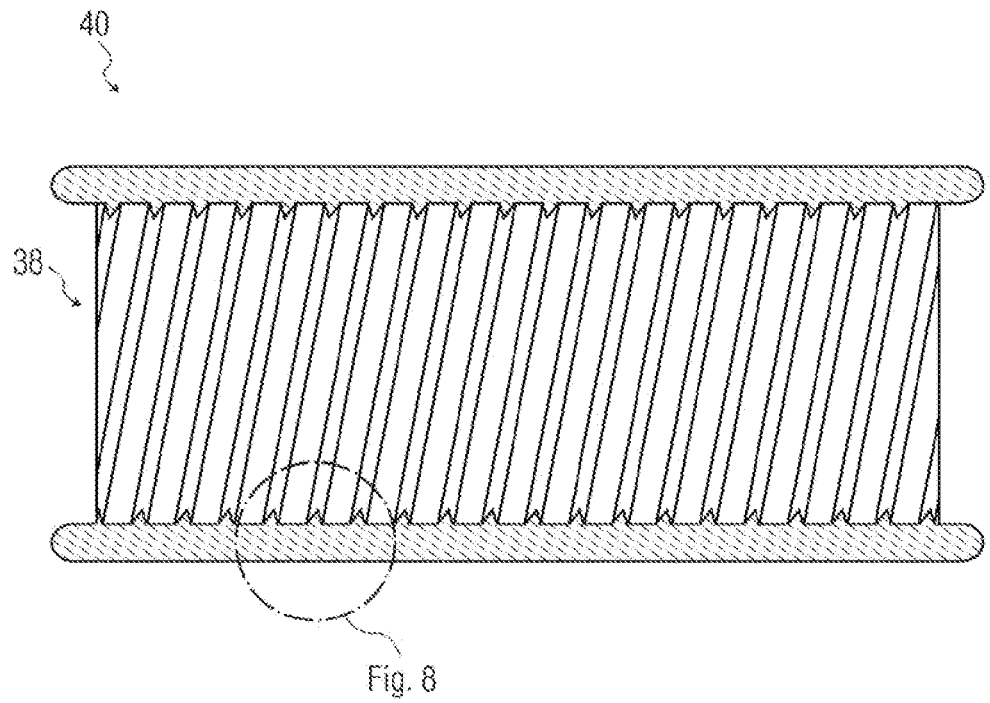
FIG. 7 shows in cross section an electromagnetic grating surface on the inner face of a drift tube that can be used in the source of interrogating radiation of the system of FIG. 1.
Figure 8:
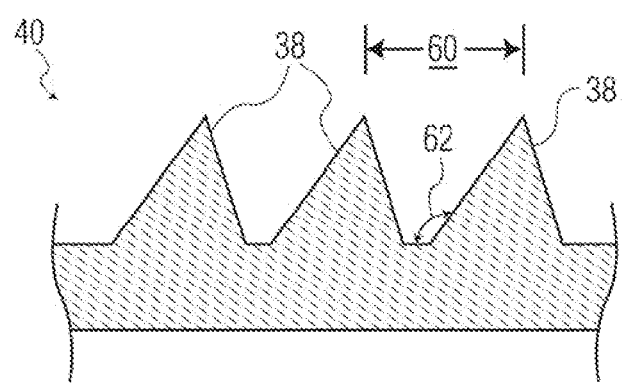
FIG. 8 is an enlarged detail view of that portion of FIG. 7 shown in a circle marked FIG. 8, which is not shown to scale.

The grating surface 38 of FIGS. 7 and 8 can be formed by many methods. Referring to FIG. 8, the spacing 60, face angle 62 and geometry of the grating 38 all are determinants in the frequency achieved. It has been determined that the preferred embodiment of the grating 38 of the drift tube grating is an internal thread as best shown in FIGS. 7 and 8. By altering the thread parameters, the output frequency is changed. The ends of the Drift Tube 40 are radiused to minimize formation of undesirable electric field perturbations inside the Resonant Cavity.

Current Regulator 90

As mentioned above, a suitable interrogating radiation source 14 (FIG. 1) for the system 10 of FIG. 1 is a Magnetically Insulated Linear Oscillator that has been enhanced by the addition of a Cylindrical Smith-Purcell structure, such as CSP-MILO apparatus 30 of FIG. 2. It is necessary to carefully regulate the output power of the Interrogating radiation source 14, which is accomplished by limiting the current fed to the cathode 42. In current regulator circuit 90 of FIG. 6, introduced above, current through a main modulating device 92 connected between an input node 94 and an output node 96 is modulated in response to a control device 100.

Current regulator circuit 90 of FIG. 6 is somewhat analogous to the classic FET (Field Effect Transistor) current regulator found low voltage power supplies. The problem addressed by current regulator circuit 90 is that there are no solid state or conventional vacuum tube devices that are capable of operating in the voltage or current regimes contemplated for this design. Accordingly, the main modulating device 92 preferably is a cold cathode field emission controllable electron tubes of triode, tetrode or pentode structure. The main modulating device 92 may have the geometrical structure shown in FIG. 15 and as further described in above-mentioned U.S. Pat. No. 4,950,962. Alternatively, the main modulating device 92 may comprise a high voltage semiconductor device such as a thyristor. The control device 100 may be implemented in the same way as main modulating device 102 to reduce diversity of parts required, or may be implemented by a device with relatively lesser voltage and current requirements.

In current regulator circuit of FIG. 6, the following description of operation assumes a positive voltage source on input node 94. A resistor 98 establishes a bias voltage for the grid of main modulating device 92, shown as a first electron tube, which functions as a series current regulator. The main modulating device 92 is functionally analogous to a FET in this circuit.

The current flowing from the modulating device 92 flows through a shunt resistor 102 so as to develop a voltage across such resistor. This voltage is fed through a voltage divider comprised of first and second voltage divider resistors 104 and 106, respectively. Control device 100 for main modulating device 92 is preferably a second electron tube used as a control tube, and may be a cold cathode field emission electron tube. The grid of control device 100 is connected to the junction of the first and second voltage divider resistors 104 and 106. A control voltage is applied to the other side of resistor 104; that is to node 108. The ratio between the voltage of shunt resistor 102 and the reference voltage produced by the resistive voltage divider on node 108 determines the degree of conduction of control device 100, which, in turn, controls the conduction of main modulating device 92. A capacitor 110 establishes a time constant with resistor 104 to ensure that the circuit stays in conduction up to the zero-crossing point. By adjusting the values of the reference voltage on node 108 and the resistor values of voltage divider formed from resistors 104 and 106, different current-regulation modes can be implemented.

Exposing Object 12 to Radiation

Referring again to FIG. 1, in the preferred embodiment, an interrogating signal 16 is provided which simultaneously contains electromagnetic radiation of sufficient bandwidth in the range of approximately 10 GHz to approximately 25 THz to allow simultaneous detection of a plurality of signals at a plurality of frequencies, each signal being at some amplitude, which collectively provide a unique spectral signature of a material whose detection is desired. This EM beam 16 preferably has as low a power as possible while still maintaining a desired signal-to-noise ratio, and is typically below one to five Watts. A Cylindrical Smith-Purcell Enhanced Magnetically Insulated Linear Oscillator (CSP-MILO) 30 (FIG. 2), as described above, is the preferred source, since it meets the frequency and output requirements as previously defined. Referring again to FIG. 5, as mentioned above, the output beam is preferably fully or partially collimated, or focused by an off-axis parabolic reflector 54.

Detection of Presence and Amount of Foreign or Native Material

Referring to FIG. 1, detection of the presence and amount of foreign or native material is preferably accomplished by use of a detector system 20 using a pyroelectric detector. While it is possible to include image detection in this invention, in the preferred embodiment, this is not done in deference to prevailing sentiments about the invasive and offensive nature of screening of human beings for foreign materials. Prevailing sentiments against imaging of the human body has been repeatedly observed in the testing and use of prior art mm Wave imaging systems for screening. Elimination of the imaging function in a preferred embodiment eliminates the foregoing concerns of the general public. Further, the implementation of the spectroscopic detection capability provides significantly more useful information to the operator. Additionally, the levels of false positive and false negative results are both reduced by using spectroscopic detection.

A preferred embodiment comprises a detector system 20 (FIG. 1) made from a Quantum Ferroelectric (QFE) material. QFE detectors are broadband and are capable of operation at room temperature. QFE detectors are distinguished from conventional detectors in that incident photons at temperatures above the temperature of the detector photocathode are represented as positive charges, while photons at temperatures below the temperature of the photocathode are represented as negative charges. The only place in the spectrum where the QFE detector does not work is when the incident photons are at the same temperature as the photocathode. The temperature of the photocathode can be shifted by heating or cooling a small amount to shift this null region. A typical QFE material is a thin film of PolyVinylidene Fluoride (PVDF). PVDF is manufactured under the tradenames of KYNAR and HYLAR. KYNAR PVDF is a product of Arkema, Inc. of Philadelphia, Pa., U.S.A., by way of example, and HYLAR PVDF is a product of Solvay Chemical S.A. of Brussels, Belgium, by way of example. Choice of a suitable detector will be apparent to a person of ordinary skill in the art based on the present specification.

Parallel Spectroscopy

Figure 9:
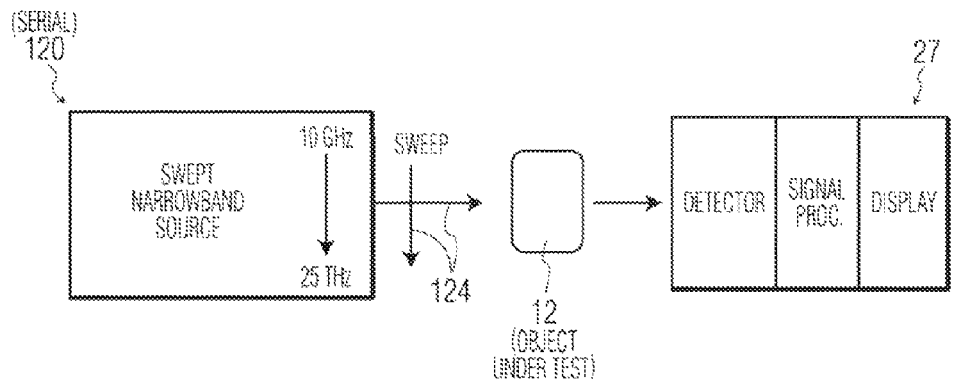
FIG. 9 shows in block diagrams a prior art Serial mode spectroscope.
Figure 10:
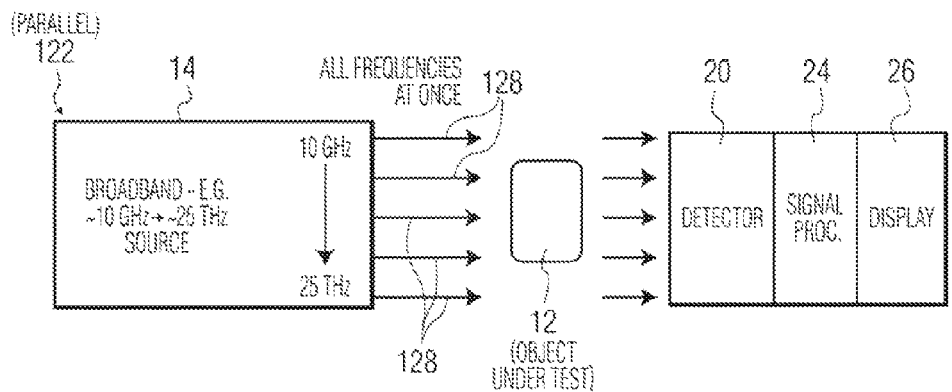
FIG. 10 shows in block diagrams a parallel mode spectroscope, which may be used in the system of FIG. 1.

FIG. 9 shows a serial mode spectroscope 120 according to the prior art, and FIG. 10 shows a parallel mode spectroscope 122 preferably used in the invention. In the serial mode spectroscope 120 of FIG. 9, an object 12 under test is swept with sequential scans over a range of frequencies, as indicated by arrows 124. Block 127 indicates the functions of detecting of a modified signal, signal processing and display. However, the use of a serial mode spectroscope 120 results in slow speed of data acquisition and processing. To increase the speed of data acquisition and processing, so as to make the invention more practical and cheaper to use, it is desirable to convert the data received from scanning object 12 under test into a parallel format as early as possible in the signal processing process; this enables the more mathematically-intensive operations to be conducted in parallel. This is indicated in FIG. 10 by arrows 128, which indicate the illuminating (or scanning) of object 12 under test by all or many frequencies of interrogating radiation simultaneously. This speeds up the spectroscopic process significantly, and enables data to be presented in a three-dimensional state to the optical correlator 24 of FIG. 1 for signal processing, indicated in FIG. 10 by "SIGNAL PROC." 24. By "three-dimensional state" is meant that the data is presented as an array or matrix where each point has an integer representation of the amplitude of a detector output in response to an interrogating signal. A further definition of "three-dimensional state" is set forth below. Another reason that parallel mode spectroscopy is substantially faster than conventional serial mode spectroscopy in the context of an inventive embodiment is due to the extremely high bandwidth of the optical correlator 24 (FIG. 1) employed in the preferred embodiment. As is known to those of ordinary skill in the art, optical signal processors, such as optical correlator 24 (FIG. 1), are inherently fast and thus of high bandwidth. The choice of a specific bandwidth for illuminating an object 12 depends on the specific foreign or native materials sought, as will be apparent to a person of ordinary skill in the art from the present specification.

Parallel mode optical processors (e.g., 24, FIG. 1) have typical input-to-output throughput time for complex correlation operations on the order of 2 to 20 nanoseconds. This is the total time required for a complete correlation operation. The throughput is ultimately limited by the speed at which data can be inputted to an input spatial light modulator (SLM) (not shown in FIG. 1) of the optical correlation processor 24. Modern electronics allow thousands of correlation operations to be conducted in a matter of seconds, thus allowing more than ample time to scan, for instance, for all known threats, plus scan for contraband and a number of pathogens, including but not limited to, viruses, bacteria, proteins, prions, fungi, spores, which spread by airborne transfer.

Fluorescence Mode

Figure 11:
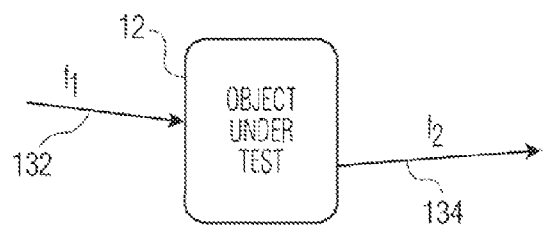
FIG. 11 shows a schematic representation of the concept of fluorescence spectroscopy that may be employed in the system of FIG. 1.

The parallel mode spectroscope 122 shown in FIG. 10 operates in the absorption mode. In addition to using a parallel mode spectroscope operating in the absorption mode, it is possible to excite the object 12 under test, as shown in FIG. 11, by radiation 132 in the same band, but at a specific frequency $f_1$ known to excite a secondary resonant radiation 134 at a frequency $f_2$ if foreign or native material with such known resonance frequency is present. This reaction produces the second radiation 134 of electromagnetic energy of known characteristics, whose identification and detection allow a more simplified data analysis. This is akin to conventional fluorescence spectroscopy but carried out at a lower frequency than with the conventional optical equivalent.

The stimulating (or interrogating) signal can be either narrowband, at or near the exact resonance frequency of the foreign materials being tested for, or can be a wideband signal that will also produce the desired secondary (i.e., stimulated) output in the presence of the mentioned foreign material in the object 12 being tested. These interrogation signals may be produced by the CSP-MILO apparatus 30 of FIG. 2 in the preferred embodiment or by other known RF sources of appropriate frequency and output power.

Three-Dimensional Data Representation

In the preferred embodiment, data is fed in parallel from points in the detector system 30 (FIG. 1) to corresponding buffers in a two-dimensional matrix data storage array 136 where each point in such two-dimensional matrix data storage array contains a numerical value equivalent to the strength of the signal received by the corresponding point in the detector. It is also possible to transfer the data in a parallel-to-serial-to-parallel manner, although this is not as efficient as the preferred embodiment.

Figure 12:
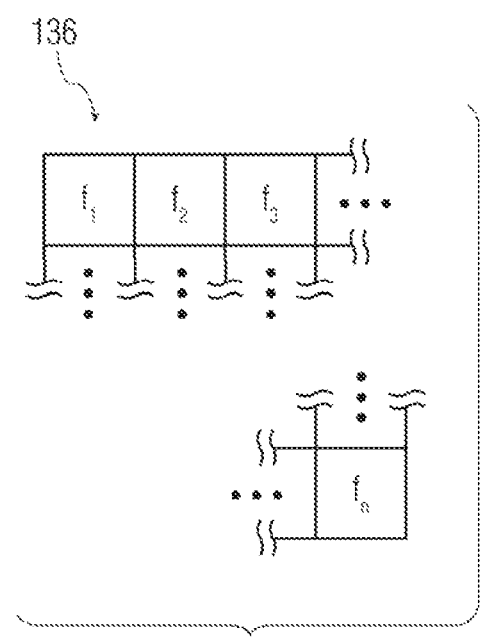
FIG. 12 shows a two-dimensional data matrix array representative of a synthetic image that may be used in the system of FIG. 1.

Each data storage site in the two-dimensional matrix data storage array 136 is capable of holding a numerical value in the range of 0 to x, where x is an integer equal to the dynamic range of the system. The distribution of data can be either raster or zigzag. The value of each buffer is representative of the amplitude of the signal from the detector at a given sampled frequency. Data formatted in this fashion is referred to as a "synthetic image." A synthetic image has no recognizable image properties, is only able to be read by a machine, and appears to the human eye as an X-Y grid of squares of varying shades of grey or varying color (another possible encoding technique). FIG. 12 shows a matrix 136 representative of the synthetic image, wherein each cell contains a numerical value which is at a frequency, such as $f_1, f_2, \ldots f_n$. As apparent from the foregoing explanation, each cell in matrix 136 could be made to appear to the human eye as having a various shade of grey or a color.

Optical Correlator

Figure 13:
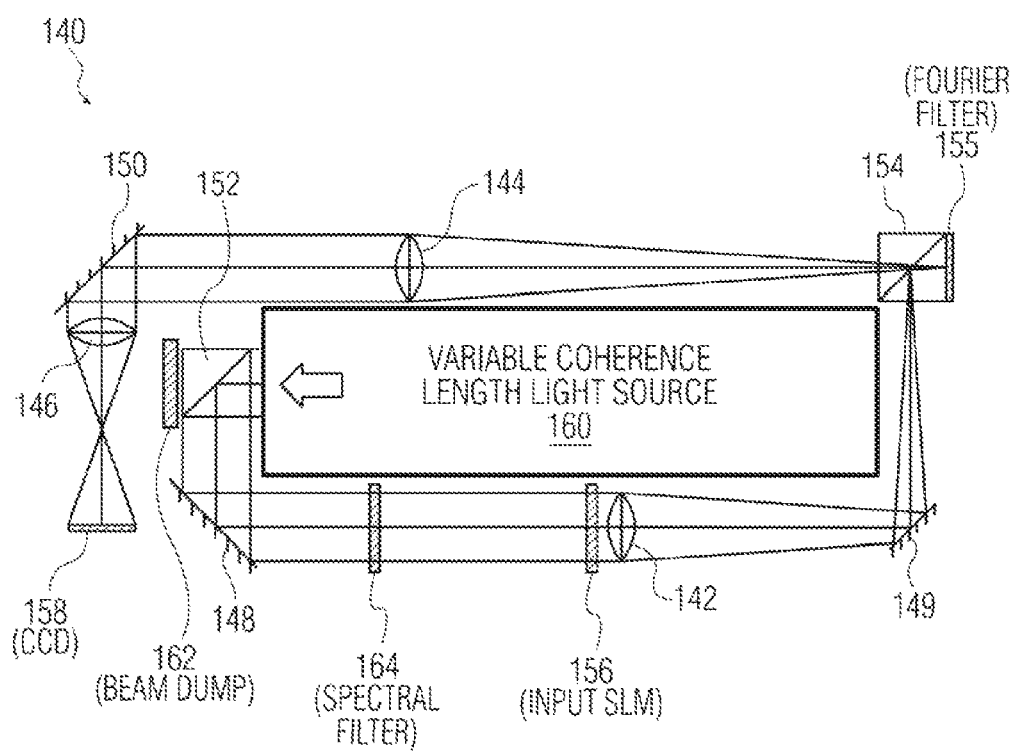
FIG. 13 shows in top plan view of an Optical Correlation Signal processor that may be used as the optical correlator in the system of FIG. 1.

Optical correlation processor 24 of FIG. 1 may be embodied by the analog optical correlator 140 described in regard to FIG. 13. An analog optical correlator is a device for comparing two signals by utilizing the Fourier-transforming properties of a lens. It has been used for target tracking and identification in missile-targeting systems. It has the advantage of having an apparent bandwidth that is substantially higher than its electronic counterpart.

While the mathematical operation performed by analog optical correlators and electronic correlators is essentially the same, their physical implementations are very different. An electronic correlator is comprised of conventional electronic circuitry mounted on printed-circuit boards. In contrast, an analog optical correlator such as shown at 140 in FIG. 13 includes lenses 142, 144 and 146, mirrors 148 and 150, polarizing beamsplitters 152 and 154 and electro-optical devices, such as input spatial light modulator (SLM) 156. The foregoing parts are used in the transition from the electronic domain, via input spatial light modulator SLM 156, to the optical domain and back to the electronic domain via a charge-coupled device (CCD) camera 158. The analog optical corr-elator 140 further includes a variable coherence length light source 160, a beam dump 162, and a monochromatizing spectral filter 164.

As general background, an analog optical correlator has an input signal which is transformed by some filter function in the Fourier domain. An example filter in the Fourier domain is a matched filter as presented to the analog optical correlator 140 by spatial light modulator 155. Such matched filter in the Fourier domain cross correlates the filter signal at 155 with an input synthetic image (e.g., 138, FIG. 12) presented to the correlator 140 at the input spatial light modulator 156. The correlation process is discussed as follows.

It is noted that the data matrix as defined herein is referred to as a three-dimensional matrix. However, in the following mathematical equations, the data matrix is shown as a two-dimensional entity [(x,y)]. This is due to the fact that the mathematical equations herein do not show the amplitude value for each element (x,y).

The cross correlation, c(x,y) of a two-dimensional signal i(x,y) with h(x,y) is:

$$c(x,y) = i(x,y) \otimes h^*(-x,-y)$$

This can be re-expressed in Fourier space as –

$$C(\xi,\eta) = I(\xi,\eta) H^*(-\xi,-\eta)$$

where the capital letters denote the Fourier transform of the lower case letter. So, the correlation can then be calculated by inverse Fourier transforming the result.

According to Fresnel Diffraction theory, a double-convex lens of focal length f will produce the exact Fourier transform at a distance f behind the lens of an object placed f distance in front of the lens. In order for the complex amplitudes to be transformed, the light source must be coherent and is typically from a laser. The input signal in the form of a digital filter is typically written onto a spatial light modulator ("SLM") (e.g., 156, FIG. 13). Optical correlation performed with a laser as the light source has certain disadvantages which include formation of artifacts and false signals due to the high coherence length of lasers. It is preferable to use a light source 160 of partial coherence length, preferably adjustable so that the optimal coherence length can be set for a particular system.

The analog optical processor 140 of FIG. 13 operates as follows. The input signal is electronically written to a first SLM 156 located at the input plane, such plane being illuminated by a light source (not shown) of appropriate coherence length. The input plane is imaged on the Fourier plane by a double-convex lens 142, where the distances from the image plane to such lens and from such lens to the Fourier plane are equal to the focal length of such lens 142. A second SLM 155 is located at the Fourier plane, such SLM being a dynamic, matched filter which selectively removes information from the input based on the Fourier characteristics of such matched filter. The resulting signal is Fourier transformed with a second lens 144, located at a distance equal to the focal length of lens 144. The resulting signal is again Fourier transformed producing the inverse transform of the Fourier plane and the output of lens 144 is imaged onto the CCD camera 158, which is located at a distance twice the focal length of lens 144. The resulting image formed on the CCD camera 158 is the input image transformed by the matched filter. The lens 146 is provided to focus the modulated, collimated light coming from lens 144 onto CCD camera 158.

As shown in FIG. 13, the optical correlation processor 140 has its optical path folded by the three mirrors 148, 149 and 150 and the two polarizing beamsplitters 152 and 154. The first beamsplitter 152 may be a cube, and performs the dual functions of folding the optical beam and polarizing it simultaneously. The second beamsplitter 154 has an SLM Fourier filter 155 optically bonded to one surface of the second beamsplitter 154 cube. This configuration allows the combination of the second beamsplitter cube 154 and second SLM 155 to act as both a folding mirror and active Fourier filter. The second SLM 155 may be optically bonded to the second beamsplitter 154 if such beamsplitter is a cube. Alternatively, the second SLM 155 may be directly formed on the appropriate surface of the beamsplitter cube 154. First, second and third mirrors 148, 149 and 150 are monochromatic dielectric stack mirrors and are used for folding the beam.

Variable coherence light source 160 is provided to allow the coherence length of the illuminating beam to be adjusted to a desired value for optimal correlation performance. The coherence length requirement varies with the specific values chosen for the optical correlation processor, but is typically in the range of 0.25 mm to 10 mm.

The input SLM 156 in the beam path prior to the second beamsplitter 154 allows the introduction into optical correlator 140 of the synthetic image 138 (FIG. 12) derived from the data taken from the object 12 under test. The Fourier filter 155 on the second beamsplitter 154 is provided with other synthetic images 138 (FIG. 12) from a reference library which preferably is stored in the host computer 26 (FIG. 1). This library contains synthetic images 138 (FIG. 9) of each threat or other foreign material or native material to be analyzed. The reference library may contain data of foreign material only, native material only, or a combination of foreign and native material.

The output of the optical correlation processor is directed to CCD camera 158 which converts the optical signal back into an electronic signal for use by the host computer 26 (FIG. 1) for the Threshholding Operation described below. Preferably, no actual images of the object under test are formed in system 10 (FIG. 1) for protection of privacy of the object under test when the object is a human being, and also to keep the cost of the system to reasonable levels. But, it is possible to add an imaging function which would provide an image with detected foreign or native materials overlaid on the image.

The system 10 as described provides the capability of performing multiple Fourier operations, which includes disregarding materials that are not foreign or that are not native to an object under test.

Although the foregoing optical correlator 140 of FIG. 13 is preferred, correlators using other technologies can be used. For instance, suitable correlators include those using a digital computer and those using firmware.

Subtractive Signal Processing

One problem that is encountered in the present type of signal processing is the presence of information that is not specifically related to the detection of foreign materials or native materials, and as such constitutes a noise component. To eliminate such noise, it is possible to subtract spectra directly associated with such noise components, to simplify the remaining data set. This is referred to herein as "subtractive signal processing," which is a technique by which one data set is subtracted on a point-by-point basis from a second data set. For example, when screening or analyzing an object for foreign material, a data set containing spectral information of purely native material in an object is subtracted from a data set that has combined information of native material in the object and any associated foreign. The result of this process is a spectra of only any associated foreign material contained in the original sample data set.

Threshholding Operation

Once correlation peak(s) of fully processed data are obtained as described above, it is desirable to compare their amplitudes to those contained in the reference spectra in the signature library. Any peak rising above a given level will trigger an indication in the operator's interface.

Figure 14:
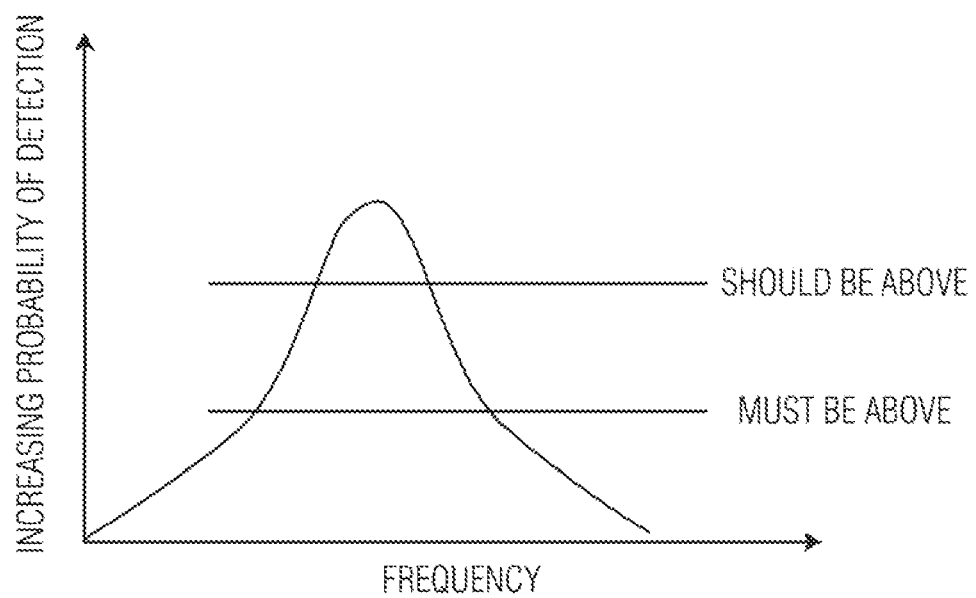
FIG. 14 shows a graph depicting a thresholding operation.

The presence of multiple peaks can be displayed in a similar fashion to the way single peaks are handled. FIG. 14 shows a graph depicting the Threshholding operation. As shown in FIG. 14, the threshholding conditions are satisfied if the signal is at least above the "MUST BE ABOVE" level, which is an exemplary indication for searching the object by other techniques, such as manually. The signal is given extra weight if it is at least above the "SHOULD BE ABOVE" level, which is an exemplary indication that the object should be seized since it may definitely have a foreign material, for instance. Thus, a "MUST BE ABOVE" signal indicates the likely presence of foreign or native material, while a "SHOULD BE ABOVE" signal indicates the definite presence of foreign or unexpected low amount of native material.

Threshholding techniques other than those shown in FIG. 14 can be used if desired.

Providing Detection Results

The results of the foregoing determination of presence of foreign material can be used in various ways. For instance, the results can be provided to a human operator, or presented to a secondary system for taking automated corrective action.

There are a number of possible operator interface techniques that can be applied to the current invention. These techniques range from a single pilot light indicating that further attention to this particular object under test is required, to a bank of lights indicating the presence of specific foreign materials of interest, to numerical displays of the quantities of specific foreign materials of interest, to full spectrum plotted displays. Or, the results can be presented to a secondary system in a fully automated machine-level interface. The choice of interface technique varies with the specific reason for use of this system, the level of proficiency of the operator, etc.

Figure 15:
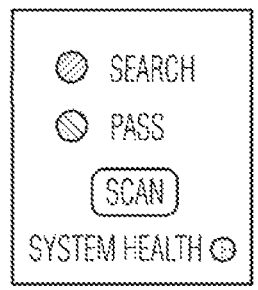
FIGS. 15-19 show several possible operator interface control panels that can be used in the display of the system of FIG. 1.
Figure 16:
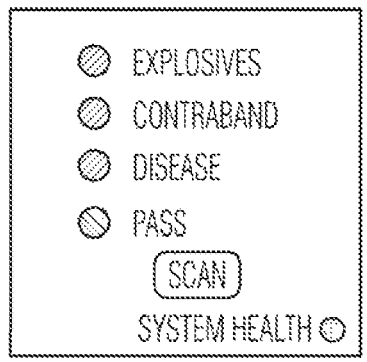

FIG. 15 shows several possible operator interface control panels. In FIG. 16, five potential human operator interfaces are shown. FIG. 15 shows the simplest version. It has just two major indicator lights, Pass and Search. When searching for foreign material, an illuminated Pass indicator light indicates that the object under test does not contain any foreign material. When searching for native material, an illuminated Pass indicator light indicates that an acceptable amount of native materials is present. If the Search indicator light is illuminated, the object under test should be subjected to close scrutiny.

FIG. 16 is slightly more sophisticated. It has four major indicator lights: Explosives, Contraband, Disease and Pass. This version is oriented specifically towards passenger screening applications, although other applications are possible. The Pass function is the same as in FIGS. 15 and 16. The three indicator lights (for Explosives, Contraband, and Disease) illuminate if any foreign materials falling within those descriptions are detected. It is obvious, that any of these categories could be any desired chemical material, and that the number of indicator lights for this function is not limited to three.

Figure 17:
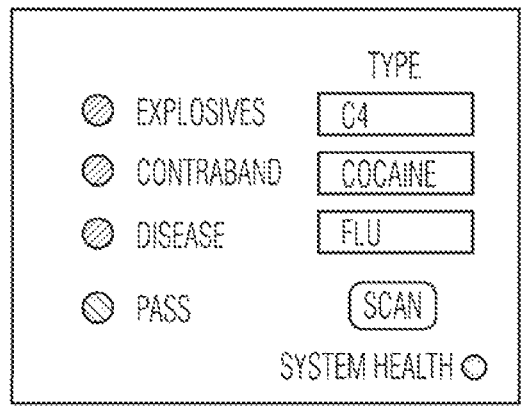

FIG. 17 is an expansion of the design of FIG. 16. It adds alphanumeric displays to indicate which specific foreign material in each category is detected.

Figures 18, 19:
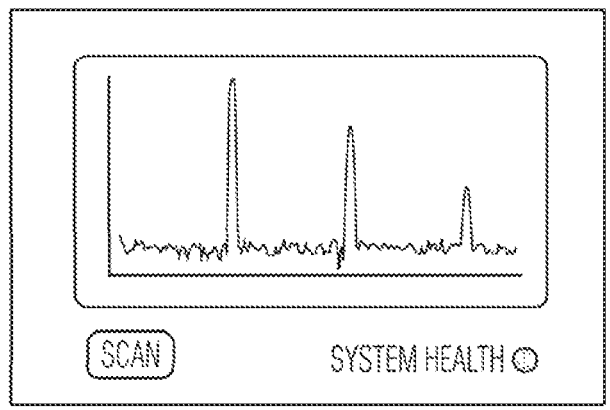

FIG. 18 expands on the design of 17. It adds displays that provide numerical quantification of the amount of a given foreign material is detected.

FIG. 19 shows a totally different human operator interface approach. It is designed for a sophisticated operator who is trained to recognize specific spectra of a wide range of foreign materials. This display is comparable to that of a typical laboratory-grade spectroscope and display the spectrum directly.

It is obvious that many other variations and combinations are possible for the human operator interface. This function is tailored to meet level of competence of the operator and the specific circumstances of the screening task.

Comparison with Known Material in Native Analysis Mode

Although some aspects of the foregoing description have emphasized detection of presence and amount of foreign material, for instance, another feature of the invention is to compare an object under test with a known object that lacks foreign material. In this regard, it is desirable to be able to quantify the amounts of materials native to an object when testing or analyzing sample objects, since there are many situations where there is no a priori knowledge of the potential presence of foreign materials, thus making a search for them difficult if not impossible. If, however, there is a priori knowledge of the exact amount of native material, a signal that does not match that criteria successfully inferentially indicates the presence of foreign material, even though a system cannot specifically identify what is the foreign material. In this context, matching of signals is determined by a Threshholding operation such as described above.

As an example of the foregoing feature of the method, one may compare a pharmaceutical object under test with a reference pharmaceutical of known active pharmaceutical ingredient to see if the active pharmaceutical ingredient of the object under test matches that of the reference pharmaceutical.

In the foregoing comparison, for best accuracy, both the composition, and weight, of the active pharmaceutical ingredient of a pharmaceutical object are compared to the reference. However, a comparison of only the composition of the active pharmaceutical ingredient of the object may be useful as well, although with possibly less accuracy. While this approach does not provide specific information regarding the nature of any deviation from a perfect match of the object under test and the reference object, the mere deviation in composition or in composition and amount, is sufficient to trigger an alarm or otherwise indicate the deviation. In this context, a "perfect match" is within the manufacturing tolerance of the object being tested. This level of testing can be conducted at very high speeds, commensurate with modern production line technologies. A pharmaceutical object, for instance, that fails to match a reference object can then be subjected to further analytical techniques to specifically identify the reason for deviation, such as inclusion of foreign material. This can be accomplished with the system 10 of FIG. 1 by analyzing for foreign material. Similar techniques can be applied to other native materials.

Simultaneous Analyses Mode

A further extension of the foregoing concept of comparing an object under test with a known reference object allows for simultaneous analyses for both native and foreign materials.

Sequential Analyses Mode

A still further extension of the foregoing concept of comparing an object under test with a known reference object starts with undertaking such comparison, as detailed under "Comparison with Known Material in Native Analysis Mode." If it is determined that the object under test deviates from the known reference object, then a sequential analysis is undertaken, by changing the operating mode of the inventive system, to then analyze for specific foreign materials.

Learning Mode of Operation for Reference Library

At times, it is desirable to add data for other materials to the reference library. This could be either when the system 10 (FIG. 1) is first initiated following construction, or an any point when it is necessary to add additional data for other materials to the library. This most expeditious method of creating new library data is as follows: A reference sample of the material is exposed to interrogating radiation in the system 10 of FIG. 1. An output is taken directly from the matrix data 136 (FIGS. 1 and 12) and is entered into the library by the host computer 26 (FIG. 1). While there are other methods of achieving the same end result, the aforementioned is the preferred method.

The following list of drawing reference numbers has three columns. The first column includes drawing reference numbers; the second column specifies the parts associated with the reference numbers; and the third column mentions a preferred material (if applicable) for the parts.

| # | ITEM | PREFERRED MATERIAL |
|---|---|---|
| 10. | System | Various |
| 12. | Object | Various |
| 14. | Source of Interrogating Radiation | Various |
| 16. | EM Radiation | EM Radiation |
| 18. | Radiation | EM Radiation |
| 20. | Detector System | QFE material |
| 24. | Optical correlator | Various |
| 26. | Host computer and display | Various |
| 30. | CSP-MILO | Electron Tube |
| 34. | Arrangement | Electron beam and plane grating |
| 36. | Arrangement | Electron beam and cylindrical grating |
| 38. | Cylindrical grating | Conductive metal |
| 40. | Drift tube | Conductive metal |
| 42. | Cathode | Carbon |
| 44. | Grid | Conductive metal |
| 46. | Travelling wave electron gun (TWEG) | Carbon and metal |
| 48. | Anode | Conductive metal |
| 50. | Window | RF transparent material |
| 52. | Beam | EM radiation |
| 54. | Reflector | Conductive metal |
| 56. | Cavity section | Conductive metal |
| 60. | Spacing | n.a. |
| 62. | Face angle | n.a. |
| 90. | Current regulator circuit | Electronic circuit |
| 92. | Main modulating device | Electron tube |
| 94. | Input node | Circuit element |
| 96. | Output node | Circuit element |
| 98. | Resistor | Circuit element |
| 100. | Control device | Electron tube |

-continued

| # | ITEM | PREFERRED MATERIAL |
|---|---|---|
| 102. | Shunt resistor | Circuit element |
| 104. | Resistor | Circuit element |
| 106. | Resistor | Circuit element |
| 108. | Node | Circuit element |
| 110. | Capacitor | Circuit element |
| 120. | Serial mode spectroscope | Various |
| 122. | Parallel mode spectroscope | Various |
| 124. | Arrows | n.a. |
| 127. | Block | Various |
| 128. | Arrows | n.a. |
| 132. | Radiation | EM radiation |
| 134. | Secondary resonant radiation | Fluorescence radiation |
| 136. | Two-dimensional matrix data storage array | Electronics |
| 138. | Synthetic image | Digital data |
| 140. | Optical correlator | Various |
| 142. | Lens | Typically glass |
| 144. | Lens | Typically glass |
| 146. | Lens | Typically glass |
| 148. | Mirrors | Typically dielectric stack |
| 149. | Mirrors | Typically dielectric stack |
| 150. | Mirrors | Typically dielectric stack |
| 152. | Polarizing beamsplitter | Typically glass and dielectric stack |
| 154. | Polarizing beamsplitter | Typically glass and dielectric stack |
| 155. | Fourier filter | Electro-optical device |
| 156. | Input spatial light modulator (SLM) | Electro-optical device |
| 158. | Charge-coupled device (CCD) | Electro-optical device |
| 160. | Variable coherence length light source | Electro-optical device |
| 162. | Beam dump | Various |
| 164. | Spectral filter | Typically dielectric stack on glass |

The foregoing describes a spectroscopic method and system capable of near real-time operation for screening purposes such as those described above. Six modes of operation that have been described are: (1) foreign material analysis or screening mode; (2) native material analysis or screening mode; (3) sequential modes of operation of the inventive system; (4) a simultaneous mode of operation for analyzing or screening for both native and foreign materials; (5) fluorescence mode; and (6) learning mode for acquiring a library of matrix data for use when scanning subsequent objects.

While the invention has been described with respect to specific embodiments by way of illustration, many modifications and changes will occur to those skilled in the art. For instance, a system of the complexity of the current invention will have a plurality of operating modes in addition to the various modes described above. It is, therefore, to be understood that the appended claims are intended to cover all such modifications and changes as fall within the true scope and spirit of the invention.

What is claimed is:

1. In connection with an object having native material and potentially having foreign material, a method for detecting one or both of said native material and said foreign material by parallel-mode spectroscopy, comprising:
 a) parallel-mode data acquisition comprising:
  i) producing an interrogating signal containing electromagnetic radiation;
  ii) exposing said object and any associated foreign material to said interrogating signal so as to cause interaction between said signal and said object and any associated foreign material; and
  iii) detecting a modified signal resulting from the interaction of said interrogating signal with the object and any associated foreign material;
  iv) said interrogating signal simultaneously containing electromagnetic radiation of sufficient bandwidth in the range of approximately 10 GHz to approximately 25 THz to allow simultaneous detection of the modified signal at a plurality of frequencies, the modified signal having respective amplitudes at different frequencies, which collectively provide a unique spectral signature of a material whose detection is desired;
 b) signal processing and data reduction, comprising:
  i) processing said modified signal to feed data points resulting from said a data matrix storage array representative of at least any foreign or native material associated with the object, wherein each point in the two-dimensional data matrix storage array contains a respective representation of an amplitude of the modified signal at a given sampled frequency;
  ii) providing a reference library of data representing known chemical or biological materials of interest;
  iii) following said processing said modified signal and said providing a reference library of data, using correlation technique to compare said data matrix to said reference library; and
 c) providing the results of the foregoing comparison by indicating a likelihood of presence of foreign material or native material if an associated correlation peak from said correlation technique reaches or exceeds a threshold level, and by indicating a likelihood of absence of foreign or native material if an associated correlation peak from said correlation technique does not reach said threshold level.

2. The method of claim 1, wherein the correlation technique comprises using a parallel-mode optical correlator.

3. The method of claim 1, wherein the signal processing and data reduction comprises determining whether any correlation peaks produced rise to a sufficient level as to indicate presence and amount of foreign or native material associated with said object.

4. The method of claim 1, wherein:
 a) the reference library of data represents an object of known composition and weight;
 b) the signal processing and data reduction comprises determining whether said two-dimensional data matrix storage array matches the reference library of data with respect to composition; and
 c) providing the results of the foregoing determination.

5. The method of claim 4, wherein the signal processing and data reduction comprises determining whether said two-dimensional data matrix storage array matches the reference library of data with respect to both composition and weight.

6. The method of claim 5, wherein the reference library of data relates to only native material.

7. The method of claim 5, wherein the reference library of data contains a plurality of data of both foreign and known materials, allowing for a plurality of operating modes.

8. The method of claim 1, further comprising disregarding materials native to said object.

9. The method of claim 1, wherein the interrogating signal simultaneously contains electromagnetic radiation of sufficient bandwidth in the range of approximately 10 GHz to 25 THz and to allow simultaneous detection of the modified signal at a plurality of frequencies that collectively cover the resonant frequencies of anticipated foreign or native materials.

10. The method of claim 1, wherein said producing the interrogating signal of electromagnetic radiation is accomplished by passing insulated linear oscillator, wherein a cylindrical axis of the drift tube is aligned between an electron gun and an anode of said oscillator, and wherein the drift tube contains a cylindrical grating ruled on an interior surface of the drift tube.

11. The method of claim 1, wherein:
   a) said processing said resulting signal comprises processing said resulting signal to produce a two-dimensional data matrix storage array representative of the combined chemical composition of the object and any associated foreign or native materials; and
   b) further comprising the use of subtractive signal processing technique to extract the spectrum or spectra of interest from a broadband interrogating signal containing information of the object and any associated foreign or native material.

12. The method of claim 1, wherein:
   a) the interrogating signal comprises a resonant interrogating signal which provokes a unique, known secondary reaction from one or more specific chemical materials corresponding to one or both said native material and said foreign material if one or both said materials are present, wherein said secondary reaction produces radiation of electromagnetic energy of known characteristics; and
   b) said detecting includes detecting said secondary reaction.

13. The method of claim 1, wherein the process is configured to screen for native material.

14. The method of claim 1, wherein said signal processing and data reduction further comprises analyzing the modified signal only at specific frequencies which relate to the fluorescence emission of said material.

15. The method of claim 1, wherein a learning mode for the reference library is enabled by extracting data directly from said two-dimensional data matrix storage array and entering it into said reference library.

16. The method of claim 1, wherein said respective representation is a shade of gray or one of a range of varying colors.

17. System for producing electromagnetic radiation with enhancement from a cylindrical Smith-Purcell structure, comprising:
   a) a magnetically insulated linear oscillator having a cathode of an electron gun spaced from an anode, with a resonant cavity situated between the electron gun and said anode; and
   b) a drift tube positioned within said resonant cavity, wherein a cylindrical axis of the drift tube is aligned between said electron gun and said anode;
   c) the drift tube being enhanced by containing a cylindrical Smith-Purcell grating ruled on an interior surface of the drift tube; and
   d) a current limiter configured to limit current to said cathode, comprising:
      i) a main modulating device for modulating current provided to said cathode; said main modulating device comprising a cold cathode field emission electron tube; and
      ii) a control device connected to a gate of the main modulating device;
      iii) a control node of the control device being coupled to receive a bias voltage that depends on an external control voltage.

18. The system of claim 17, wherein said bias voltage is created as the mid-point of a resistive voltage-divider network connected between said external control voltage and a voltage that depends on the current flowing through the main modulating device.

19. The system of claim 17, wherein said cylindrical Smith-Purcell grating ruled on an interior surface of the drift tube comprises an internal thread.

* * * * *